(12) United States Patent
Jorgensen et al.

(10) Patent No.: US 6,518,228 B1
(45) Date of Patent: Feb. 11, 2003

(54) ULTRA-MILD, CLEAR, AQUEOUS, FOAMABLE SKIN CLEANSER

(75) Inventors: Lise W. Jorgensen, Trumbull, CT (US); Richard L. McManus, Shelton, CT (US); Bryan P. Murphy, Monroe, CT (US); Sharon L. Polanski, Fairfield, CT (US); Robert D. Sabin, Newtown, CT (US)

(73) Assignee: Clairol Incorporated, Stamford, CT (US)

( * ) Notice: Subject to any disclaimer, the term of this patent is extended or adjusted under 35 U.S.C. 154(b) by 0 days.

(21) Appl. No.: 09/320,895

(22) Filed: May 27, 1999

(51) Int. Cl.$^7$ .............................. A61K 7/48; C11D 3/37; C11D 7/32

(52) U.S. Cl. .................. 510/130; 510/135; 510/137; 510/159; 510/405; 510/433; 510/434; 510/437; 510/477; 510/488; 510/501; 510/503; 424/401; 514/844; 514/845

(58) Field of Search ................. 510/130, 135, 510/137, 159, 405, 433, 434, 437, 477, 488, 501, 503; 424/401; 514/844, 845

(56) References Cited

U.S. PATENT DOCUMENTS

| | | | |
|---|---|---|---|
| 4,968,450 A | 11/1990 | Kamegai et al. | 252/545 |
| 5,271,530 A * | 12/1993 | Uehira et al. | 222/190 |
| 5,336,497 A | 8/1994 | Guerrero et al. | 424/410 |
| 5,337,929 A | 8/1994 | Van der Heijden | 222/402.18 |
| 5,387,372 A * | 2/1995 | Su | 252/544 |
| 5,409,706 A | 4/1995 | Ramirez | 424/401 |
| 5,429,279 A | 7/1995 | Van der Heijden | 222/402.18 |
| 5,443,569 A | 8/1995 | Uehira | 222/190 |
| 5,679,324 A | 10/1997 | Lisboa et al. | 424/45 |
| 5,693,604 A | 12/1997 | Su | 510/499 |
| 5,804,207 A * | 9/1998 | Dubief et al. | 424/401 |
| 5,869,071 A | 2/1999 | Wieselman | 424/401 |
| 5,888,951 A | 3/1999 | Gagnebien et al. | 510/130 |

FOREIGN PATENT DOCUMENTS

| | | | |
|---|---|---|---|
| EP | 0 566 340 A1 | 10/1993 | |
| FR | 2 731 616 A1 | 3/1995 | |
| JP | 4-173729 A | 6/1992 | A61K/7/50 |
| JP | 5-63520 B | 9/1993 | A61K/7/50 |
| JP | 9-125089 A | 5/1997 | A61K/7/50 |

OTHER PUBLICATIONS

Amino acid based surfactant Amisoft, Ajinomoto No Date Given.
CAPIGEL *98 Liquid Gelling Agent, SEPPIC Mar. 1, 1998.
Richard Dodwell et al, Pemulen© Polymeric Emulsifiers: What they are, how they work, Cosmetic and Toiletries Manufacture No Date Given.
Gregg A. Nicoll et al, The relative sensitivity of two arm–wash test methods for evaluting the mildness of personal washing products, J. Soc. Cosmet. Chem., 46, 129–140 (May/Jun. 1995).

* cited by examiner

Primary Examiner—Yogendra N. Gupta
Assistant Examiner—Brian P. Mruk
(74) Attorney, Agent, or Firm—Charles J. Zeller

(57) ABSTRACT

Aqueous compositions containing about 0.5–10% of at least one salt of a fatty acid amide of an amino acid, and about 0.05–0.2% of a salt of an acrylates/$C_{10-30}$ alkyl acrylate crosspolymer, or about 0.1–0.75% of a salt of acrylates copolymer, are clear, foamable and ultra-mild on skin. When dispensed by a pump sprayer the compositions afford a dense, uniform, stable foam which when spread on the skin gives an elegant cushioning foam pad effect between the hand and skin.

17 Claims, No Drawings

ULTRA-MILD, CLEAR, AQUEOUS, FOAMABLE SKIN CLEANSER

This application relates to skin cleansers. More particularly it relates to clear, aqueous, foamable skin cleansers which when tested in accordance with the procedure specified herein qualify as being ultra-mild to the skin.

Sprayable, aqueous, body cleansing compositions are known in the art. Several have been commercialized. Ponds markets Clear Solutions' CLAIRES as a deep pore foaming cleanser. It produces an inelegant foam that is non-uniform as evidenced by large air bubbles.

STRIDEX Self Activated Antibacterial Foaming Wash is marketed by Blistex Inc. The foam produced by this product is non-uniform. Substantially larger bubbles are evident throughout the foam decreasing the foam density. According to its label the product contains disodium cocoyl glutamate and sodium cocoyl glutamate, sodium lauroyl sarcosinate and cocamidopropylbetaine. No thickener appears to be present.

Bobbi Brown Professional Cosmetics markets Bobbi Brown Essentials Gentle Foaming Cleanser. The product contains, among other ingredients, sodium laureth sulfate, cocoamidopropyl betaine, PEG-7 glycerylcocoate, decylpolyglucose and PVP. The product produces a foam that is denser than that produced by the aforementioned products, however larger bubbles are evident and the foam feels tacky.

All of the aforementioned products employ the commercially available Airspray pump foamer to deliver their compositions.

The prior art is repleat with patents directed to body cleansers. For example Su U.S. Pat. No. 5,693,604, issued Dec. 2, 1997, discloses aqueous body cleansing compositions containing, as surfactants, amphocarboxyglycinate salt, a compound of the formula $R^1-(OCH_2CH_2)_m-OSO_3^-Y^+$ and soap. The compositions also contain a long chain acylated hydrolyzed protein salt and an acylglutamate salt. Su's U.S. Pat. No. 5,387,372, issued Feb. 7, 1995, discloses high foaming compositions for cleansing the body. The compositions comprise a first amphocarboxyglycinate surfactant, a second surfactant having the formula $R^1-(OCH_2CH_2)_m-OSO_3^-Y^+$, a soap, an acylated hydrolyzed protein salt, and an acylglutamate salt. Patentee teaches that the compositions should have a viscosity that is pleasing to the feel but still allows a proper quantity of formulation to be readily delivered through an appropriately sized aperture of a hand pump delivery apparatus. Patentee further teaches that a thickening agent can be used. Examples of thickener modifiers that can be employed include cellulosic polymers and the acrylic polymers and copolymers.

It is evident from the above that the formulations of the prior art are complex in that they contain multiple surfactants and employ numerous foam stabilizing ingredients.

There is need for a simple formulation of a clear, aqueous, foamable cleanser that is ultra-mild to the skin (as opposed to mild). A simple composition containing a reduced number of surfactants and foam stabilizing agents offers less potential for skin sensitivity and irritation.

It is difficult to formulate an aqueous skin cleanser which combines clarity and foamability and yet is ultra-mild to skin. The present inventors have succeeded in producing such compositions.

The compositions of the present invention comprise as a cleanser a salt of a fatty acid amide of an amino acid, preferably acylglutamate and most preferably triethanolamine cocoylglutamate. The salt of the fatty acid amide of an amino acid is present in the composition of the invention in an amount of from about 0.5 to about 10% by weight based on the total weight of the composition. Preferably, the salt of the fatty acid amide of an amino acid is present in an amount of from about 1 to about 6% and, most preferably, from about 2 to about 5%. Typically, the compositions herein have a pH of from about 4.5 to about 8.5, preferably 5 to about 7.5, most preferably about 5 to about 7.

It should be noted that as used herein, unless indicated otherwise, percent is percent by weight, based on the total weight of the composition.

Acylalaninate is another salt of a fatty acid amide of an amino acid that can be employed in the composition of the invention. Preferably the acylalaninate is triethanolamine cocoylalaninate. The acylalaninate is employed in amounts comparable to that employed for acylglutamate.

A mixture of salts of fatty acid amides of amino acids can be employed. For example, a mixture of acylglutamate and acylalaninate can be employed as the surfactant in the composition of the present invention.

The second component of the composition of the present invention is a salt of acrylates copolymer or a salt of acrylates crosspolymer. Preferably a salt of acrylates/$C_{10-30}$ alkyl acrylate crosspolymer is employed.

The salt of the acrylates/$C_{10-30}$ alkyl acrylate crosspolymer, is present in the composition in an amount of from about 0.05 to about 0.2%. Preferably, it is present in an amount of from about 0.075 to about 0.13% and, most preferably, in an amount of from about 0.1 to about 0.125%.

When a salt of acrylates copolymer is employed, it is present in the composition in an amount of from about 0.1 to about 0.75%. Preferably, it is present in an amount of from about 0.2 to about 0.6% and, most preferably, in an amount of from about 0.3 to about 0.5%.

The third component present in the composition is water, preferably deionized water.

The preferred acylglutamate, namely, triethanolamine cocoyl glutamate, is the triethanolamine salt of the coconut acid amide of glutamic acid. It conforms generally to the formula:

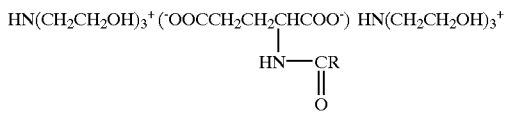

wherein RCO represents the fatty acids derived from coconut oil. This material is commercially available as Amisoft. Amisoft CT-12 is preferred. It is available as a 30% aqueous solution.

Acrylates/$C_{10-30}$ alkyl acrylate crosspolymer is a copolymer of $C_{10-30}$ alkyl acrylates and one or more monomers of acrylic acid, methacrylic acid or one of their simple esters crosslinked with an allyl ether of sucrose or an allyl ether of pentaerythritol. It is commercially available from Goodrich as Pemulen TR-1 and Pemulen TR-2. Pemulen TR-2 polymer is preferred.

It should be noted that Capigel 98, an acrylates copolymer produced by SEPPIC, can be used in lieu of Pemulen TR-1 or TR-2 except when the composition of the present invention contains a color that is sensitive to ultraviolet and requires an acidic pH. The reason for this is that at acid pH compositions of the present invention containing Capigel 98 become cloudy.

The compositions of the present invention can of course contain other surfactants and ingredients normally present in like compositions provided that such ingredients do not adversly affect the clarity of the product, its foaming characteristics, or cause the product to no longer meet the test criteria established herein for an ultra-mild skin product.

The foamable compositions of the present invention may be contained in a foam dispensing pump container comprising a container body in which the foamable composition is stored and a pump spray (also referred to as a pump foamer) generally threadably attached to the container body. The foam dispensing pump container is of the type that entrains air in the foamable composition as it is expressed through the pump sprayer, thereby causing the composition to be delivered as the stable, dense, elegant foam previously described.

Foam dispensing pump containers are known in the field. Suitable pump containers are those disclosed in U.S. Pat. No. 5,271,530 to Uehira et al. assigned to Daiwa Can Company; U.S. Pat. No. 5,429,279 to van der Heijden; and U.S. Pat. No. 5,337,929 to van der Heijden, both van der Heijden patents being assigned to Airspray International B.V. Each of these referenced patents is incorporated herein by reference. Especially preferred is Airspray pump foamer sold by Airspray International B.V., which is covered by the '929, '279 and '530 patents. This device is equipped with a screen through which the foamable compositions passes as it is delivered to the pump roamer nozzle, thereby entraining air and causing foam formation.

It has been found surprisingly that the acrylates copolymer or crosspolymer component provides foam uniformity, stability, cushion and creaminess when the composition is discharged through the pump foamer.

It should be noted as used herein a composition is ultra-mild when it causes statistically significantly less irritation and drying than currently marketed products positioned as mild to the skin and prior art products shown to be mild to the skin.

Clinical grading (dryness and erythema) and Transepidermal Water Loss (TEWL) measurements in a modified arm-wash method are used to demonstrate relevant differences.

The arm-wash method is conducted according to a modification of the procedure described by Gregg A. Nicoll et al. (The relative sensitivity of two-arm wash methods for evaluating the mildness of personal washing products, J.Soc.Cosmet. Chem., 46, 129–140(1995)).

Briefly, following a one-week washout period, diluted or neat product is applied onto the volar surface of the subjects' arms for 1 minute followed by a water rinse, 4 times daily, for 4 consecutive days. On day 5, the process is repeated for a total of 18 washes per test product. Clinical grading and instrumental measurements are conducted prior to application (baseline) and following application of product each day.

With the above in mind, and provided they do not adversely affect the clarity, foaming, or ultra-mild characterization of the product, the compositions of the instant invention can contain sunscreen(s), alphahydroxy acid(s), betahydroxy acid(s), betaglucan, hydrolyzed protein, PEG sorbitan, polysorbate(s), acylglucoside(s), and/or acylalcohol(s) or acylphosphate(s). The product can also contain germicide(s), perservative(s) (such as methylparaben), fragrance(s), humectant(s), chelating agent (s) (such as tetrasodium ethylenediamine tetraacetic acid), colorant(s), vitamin(s), antioxidant(s), antiinflammatory agent(s), and other agents typically employed in skin compositions.

Provided they do not adversely affect the clarity, foaming, or ultra-mild characterization of the product, a variety of humectants can be employed and can be present at a level of from about 0.1 to about 30%, preferably about 1 to about 8%, and more preferably about 2 to about 5% of the total formulation weight. These materials include polyhydroxy alcohols such as sorbitol, glycerin, hexanetriol, propylene glycol, hexylene glycol, and the like; polyethylene glycol; sugars and starches; sugar and starch derivatives such as alkoxylated glucose, glucosides and the like; D-panthenol; hyaluronic acid; lactamide monoethanolamine; acetamide monoethanolamine; 2-pyrrolidone-5-carboxylic acid, molecular complexes thereof, and mixtures thereof. Most preferred are glycerin and propylene glycol. Glycerin is especially preferred.

The preparation of a composition that is ultra-mild yet exhibits excellent clarity and superior foam characteristics coupled with an elegant feel when applied to the skin was a difficult task involving the screening of many surfactants and foam stabilizing agents.

Acylglutamate is known as a nonirritating surfactant however it is also known to possess very poor lathering properties. The prior art has attempted to remedy such deficiency by using it in combination with other surfactants generally along with foam stabilizers. This would increase the likelihood of skin sensitization and irritation. For example, the Su compositions contain several surfactants as well as soap, a potential skin irritant. The risk of skin sensitization and irritation increases with the use of multiple surfactants. It is believed that the Su compositions and commercially available prior art products would at best qualify as mild when tested by the procedure outlined herein.

The clear, aqueous, compositions of the present invention provide an unexpected benefit of low surfactant level, high foam thickness and uniformity while achieving a highly desirable wash lather cushion. More importantly the compositions of this invention are ultra-mild when tested by the procedure outlined herein. Still further, the compositions of the invention are preferably substantially soap free and more preferably are soap free.

As noted earlier, Capigel 98 (a liquid gelling agent available from SEPPIC) can be used in the compositions of the present invention. It is an aqueous solution of an acrylic copolymer which when neutralized in the presence of deionized water provides a translucent gel. Capigel 98 can be used, subject to the proviso outlined earlier, with or in place of Pemulen TR-1 or Pemulen TR-2.

The present invention will now be described with reference to the examples which follow. It should be understood that these examples are intended to be illustrative of the invention and are not intended to be limiting in any respect.

EXAMPLE 1

| INGREDIENTS | WEIGHT PERCENT |
| --- | --- |
| TEA-cocoyl glutamate (30% active) | 11.67 |
| Glycerin | 5.0 |
| Sodium hydroxide (50% aqueous solution) | 0.3 |
| Acrylates/$C_{10-30}$ alkyl acrylate crosspolymer (100% active) | 0.125 |
| Fragrance | 0.125 |
| Chelating agent | 0.1 |
| UV Sunscreen | 0.1 |
| Color | 0.000049 |
| Deionized Water | QS 100% |

The above formulation was prepared as follows:

About 30% of the formulation water is added to a mixing vessel and subjected to high speed mixing so as to form a vortex. The acrylates/C$_{10-30}$ acrylate crosspolymer is slowly added to the vortex. When the resultant mixture is uniform the sodium hydroxide is added to neutralize the polymer. When the mixture is uniform, the chelating agent, the TEA-cocoyl glutamate, glycerin, UV sunscreen and fragrance are added under agitation. The remainder of the sodium hydroxide is added to adjust the pH to 6.1. Then the color is added.

The resultant composition was clear and exhibited excellent foam characteristics. Foaming was enhanced by dispensing the composition from a spray bottle equipped with a screen such as is available from Airspray International B.V. Such container is covered by U.S. Pat. Nos. 5,337,929; 5,429,279 and 5,271,530. When the composition of this Example 1 was tested in accordance with the procedure outlined earlier it was determined to be classifiable as ultra-mild in so far as its effects on the skin are concerned.

EXAMPLE 2

| INGREDIENTS | WEIGHT PERCENT |
| --- | --- |
| TEA-cocoyl glutamate (30% active) | 11.67 |
| Glycerin | 5.0 |
| Sodium hydroxide (50% aqueous solution) | 0.3 |
| Acrylates/C$_{10-30}$ alkyl acrylate crosspolymer (100% active) | 0.125 |
| Aqueous oat betaglucan (1.50% active) | 0.25 |
| Fragrance | 0.125 |
| Chelating agent | 0.1 |
| UV Sunscreen | 0.1 |
| Color | 0.000101 |
| Deionized Water | QS 100% |

The above composition, was prepared as described in Example 1 except that the oat betaglucan was added prior to the addition of the polymer.

The resultant composition had a pH of 6.0. Additionally the composition was clear and when delivered through the Airspray International spray container the foam produced was dense, uniform and very stable. Moreover when spread on the skin the composition exhibited an excellent feel almost as if the hand was floating on a foam cushion on the surface of the skin. By the procedure earlier described the composition was determined to meet all criteria for an ultra-mild product insofar as its effect on the skin is concerned.

Generally when an acrylates copolymer is present, the pH of the composition should be above about 7.5 or the formulation will be hazy. When a colorant sensitive to UV is a component of the composition, the composition should have an acidic pH to prevent degradatin of the color. Accordingly, in this instance the acrylates/C$_{10-30}$ alkyl acrylate crosspolymer should be employed. A UV absorber may be incorporated to ensure long term stability of the color. An antioxidant may also be used.

The following examples demonstrate the criticality of the surfactants and thickeners employed in the composition of the present invention.

In Example 3 Amisoft CT-12 was employed as the surfactant and Capigel 98 (salt of acrylates copolymer) was employed as the thickener.

EXAMPLE 3

| INGREDIENTS | WEIGHT PERCENT |
| --- | --- |
| Glycerin | 5.00 |
| TEA-cocoyl glutamate (30% active) | 11.67 |
| Acrylates copolymer (30% active) | 1.00 |
| Preservative | 0.75 |
| Fragrance | 0.20 |
| Deionized Water | QS 100 |
| Clear | |
| Uniform foam | |
| pH 7.5 | |

The composition is prepared by premixing the acrylates copolymer with deionized water. Then adding the premix to more of the water and mixing same until uniform. Separately mixing the TEA cocoylglutamate with the remaining water and mixing until uniform. Mixing the two mixtures and when uniform adding the remaining formula ingredients and mixing until uniform. Triethanolamine is added to adjust the pH of the composition to pH 7.5.

EXAMPLE 4

| INGREDIENTS | WEIGHT PERCENT |
| --- | --- |
| TEA-cocoyl alaninate (30% active)* | 11.67 |
| Glycerin | 5.0 |
| Sodium hydroxide (50% aqueous solution) | 0.05 |
| Acrylates/C$_{10-30}$ alkyl acrylate crosspolymer (100% active) | 0.05% |
| Fragrance | 0.125 |
| Deionized Water | QS 100% |
| Clear | |
| Uniform foam | |
| pH 7.4 | |

*Amisoft ACT-12 (available from Ajinomoto)

The composition of Example 4 was prepared by the process as described in Example 1.

The compositions of Examples 1, 2, 3 and 4 were tested according to the procedure outlined earlier in this specification and were determined to be ultra-mild to skin.

What is claimed is:

1. An ultra-mild, clear, aqueous, foamable skin cleanser composition comprising by weight of the total composition
    a) from about 0.5 to about 10% of at least one salt of a fatty acid amide of an amino acid
    b) from about 0.05 to about 0.2% of a salt of acrylates/C$_{10-30}$alkyl acrylates crosspolymer
    c) water in an amount sufficient to bring the composition to 100%.

2. The composition, as claimed in claim 1, wherein the salt of a fatty acid amide of an amino acid is present in an amount of from about 1 to about 6%.

3. The composition, as claimed in claim 1, wherein the salt of a fatty acid amide of an amino acid is present in an amount of from about 2 to about 5%.

4. The composition, as claimed in claim 1, wherein the salt of a fatty acid amide of an amino acid is a salt of acylglutamate or acylalaninate.

5. The composition, as claimed in claim 1, wherein the salt of a fatty acid amide of an amino acid is triethanolamine cocoylglutamate.

6. The composition, as claimed in claim 1, wherein the salt of a fatty acid amide of an amino acid is triethanolamine cocoylalaninate.

7. The composition, as claimed in claim 1, wherein the composition contains a mixture of acylglutamate salt and acylalaninate salt.

8. The composition, as claimed in claim 1, wherein the salt of acrylates/$C_{10-30}$ alkyl acrylate crosspolymer is present in an amount of from about 0.075 to about 0.13%.

9. The composition, as claimed in claim 1, wherein the salt of acrylates/$C_{10-30}$ alkyl acrylate crosspolymer is present in an amount of from about 0.1 to about 0.125%.

10. The composition, as claimed in claim 1, further including from about 0.1 to about 30% of a humectant.

11. The composition, as claimed in claim 10, wherein the humectant is present in an amount of from about 1 to about 8%.

12. The composition, as claimed in claim 10, wherein the humectant is present in an amount of from about 2 to about 5%.

13. The composition, as claimed in claim 10, wherein the humectant is selected from the group consisting of sorbitol, glycerin, hexanetriol, propyleneglycol, hexylene glycol, polyethylene glycol, sugars and starches, glucosides, alkoxylated glucose, D-panthenol, hyaluronic acid, lactamide monoethanolamine, acetamide monoethanolamine, 2-pyrrolidone-5-carboxylic acid, molecular complexes thereof, and mixtures thereof.

14. The composition, as claimed in claim 10, wherein the humectant is glycerin or propylene glycol.

15. The composition, as claimed in claim 10, wherein the humectant is glycerin.

16. A foaming skin cleansing system comprising an ultra-mild, clear, aqueous, foamable skin cleanser composition, as claimed in claim 1, contained in a foam dispensing pump container comprising a container body in which the composition is stored and a pump foamer adapted to entrain air in the composition as it is expressed through said pump foamer, whereby the composition when pumped from said container produces a dense, uniform, stable foam which when spread on skin by hand has a density which imparts an elegant cushioning feel between the skin and hand.

17. The system of claim 16 wherein the pump foamer is provided with a screen to entrain air in the composition.

* * * * *